US012569581B2

(12) United States Patent
Seo et al.

(10) Patent No.: US 12,569,581 B2
(45) Date of Patent: Mar. 10, 2026

(54) SHOE CARE APPARATUS

(71) Applicant: SAMSUNG ELECTRONICS CO., LTD., Suwon-si (KR)

(72) Inventors: Dongpil Seo, Suwon-si (KR); Sujin Seong, Suwon-si (KR); Hakjae Lee, Suwon-si (KR); Jongwook Joo, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 351 days.

(21) Appl. No.: 18/207,353

(22) Filed: Jun. 8, 2023

(65) Prior Publication Data

US 2023/0321292 A1     Oct. 12, 2023

Related U.S. Application Data

(63) Continuation of application No. PCT/KR2021/019450, filed on Dec. 21, 2021.

(30) Foreign Application Priority Data

Jan. 29, 2021     (KR) ........................ 10-2021-0013404

(51) Int. Cl.
| | |
|---|---|
| *A61L 2/10* | (2006.01) |
| *A61L 2/26* | (2006.01) |
| *A47L 23/20* | (2006.01) |

(52) U.S. Cl.
CPC .................................... *A61L 2/10* (2013.01); *A61L 2/26* (2013.01); *A47L 23/20* (2013.01); *A61L 2202/11* (2013.01);

(Continued)

(58) Field of Classification Search
CPC .......... A61L 2/10; A61L 2/26; A61L 2202/11; A61L 2202/121; A61L 2202/122; A61L 2202/14; A47L 23/20; A47L 23/205
(Continued)

(56) References Cited

U.S. PATENT DOCUMENTS

| | | | |
|---|---|---|---|
| 9,968,697 B1* | 5/2018 | Philipps | .................... A61L 2/24 |
| 2009/0193676 A1* | 8/2009 | Shengguang | ......... A47L 23/205 34/106 |

(Continued)

FOREIGN PATENT DOCUMENTS

| | | |
|---|---|---|
| CN | 110123244 A | 8/2019 |
| CN | 105686786 B | 11/2019 |

(Continued)

OTHER PUBLICATIONS

International Search Report, PCT/ISA/210, dated Apr. 12, 2022, in International Application PCT/KR2021/019450.
(Continued)

*Primary Examiner* — Jason L McCormack
(74) *Attorney, Agent, or Firm* — STAAS & HALSEY LLP

(57) ABSTRACT

A shoe care apparatus including a cabinet, a shoe care compartment inside the cabinet, a door coupled to the cabinet and configured to open and close the shoe care compartment, a supply duct formed on a first wall of the cabinet to supply air to the shoe care compartment, a shoe support device configured to communicate with the supply duct to receive the air from the supply duct and protruding from an inner surface of the first wall of the cabinet so that shoes are placeable in the shoe care compartment, and a sterilizer installed on a second wall of the cabinet or on the door and including an ultraviolet (UV) lamp to sterilize shoes placed in the shoe care compartment.

10 Claims, 7 Drawing Sheets

(52) U.S. Cl.
CPC ... *A61L 2202/121* (2013.01); *A61L 2202/122* (2013.01)

(58) Field of Classification Search
USPC ..................................................... 250/455.11
See application file for complete search history.

(56) References Cited

U.S. PATENT DOCUMENTS

| | | | |
|---|---|---|---|
| 2011/0048474 A1* | 3/2011 | Kim ........................ | A47L 23/20 |
| | | | 134/115 R |
| 2022/0313061 A1 | 10/2022 | Kim et al. | |

FOREIGN PATENT DOCUMENTS

| | | |
|---|---|---|
| KR | 20-0394564 | 9/2005 |
| KR | 20-0425562 | 9/2006 |
| KR | 10-0934977 | 1/2010 |
| KR | 10-2010-0106162 | 10/2010 |
| KR | 10-2010-0113680 | 10/2010 |
| KR | 10-1174227 | 8/2012 |
| KR | 10-2013-0030717 | 3/2013 |
| KR | 20-2013-0004718 | 8/2013 |
| KR | 10-2013-0131958 | 12/2013 |
| KR | 10-1335362 | 12/2013 |
| KR | 10-2016-0034684 | 3/2016 |
| KR | 10-2017-0054022 | 5/2017 |
| KR | 10-1765858 | 8/2017 |
| KR | 10-1769806 | 8/2017 |
| KR | 10-2057418 | 12/2019 |
| KR | 10-2021-0085188 | 7/2021 |

OTHER PUBLICATIONS

Written Opinion, PCT/ISA/237, dated Apr. 12, 2022, in International Application PCT/KR2021/019450.
Office Action dated Feb. 3, 2025, issued in Korean Application No. 10-2021- 0013404.

* cited by examiner

SHOE CARE APPARATUS

CROSS-REFERENCE TO RELATED APPLICATIONS

This application is a continuation of International Application PCT/KR2021/019450, filed Dec. 21, 2021, and claims foreign priority to Korean application 10-2021-0013404, filed Jan. 29, 2021, the disclosures of which are incorporated herein by reference in their entireties.

BACKGROUND

1. Field

The present disclosure relates to a shoe care apparatus, and more particularly, to a shoe care apparatus capable of sterilizing shoes.

2. Description of Related Art

A shoe care apparatus is an apparatus for caring for shoes, such as drying shoes, cleaning shoes, and removing odors from shoes.

Hot air, ozone or ultraviolet light can be used to sterilize shoes in the shoe care apparatus. However, hot air may damage shoes, and ozone may adversely affect the human body even in minute amounts.

Ultraviolet rays may be harmless if they do not reach the human body in large amounts, but the temperature of an ultraviolet lamp (UV lamp) emitting ultraviolet rays may become excessively high. Therefore, there is a need to control the temperature of the UV lamp while maximizing the sterilization effect of the shoe.

SUMMARY

An aspect of the present disclosure provides a shoe care apparatus including a cabinet, a shoe care compartment provided inside the cabinet, a door coupled to the cabinet and configured to open and close the shoe care compartment, a supply duct formed on a first wall of the cabinet to supply air to the shoe care compartment, a shoe support device configured to communicate with the supply duct to receive the air from the supply duct and protruding from an inner surface of the first wall of the cabinet so that shoes are placed in the shoe care compartment and a sterilizer including an ultraviolet (UV) lamp to sterilize shoes placed in the shoe care compartment, the sterilizer installed on a second wall of the cabinet or the door.

The sterilizer is disposed within the second wall of the cabinet.

The shoe support device includes a plurality of support frames protruding in a first direction toward an inside of the shoe care compartment and spaced apart in a second direction, the sterilizer is disposed between the plurality of support frames along the second direction.

The sterilizer is installed in a center of the second wall of the cabinet.

The first wall is a side wall of the cabinet, and the second wall is an upper wall of the cabinet.

The sterilizer includes a first case coupled to the upper wall of the cabinet and in which the UV lamp is seated, a protective plate accommodated in the first case and disposed below the Ultraviolet lamp, a reflective member disposed above the UV lamp and a second case disposed above the reflective member and configured to cover the reflective member and the Ultraviolet lamp.

The shoe care apparatus may further include a plate disposed below the shoe support device and at least one reflector disposed on at least one of a third wall of the cabinet, the door, and the plate to reflect ultraviolet rays irradiated from the ultraviolet lamp.

The first wall is one side wall of the cabinet, the second wall is an upper wall of the cabinet, and the at least one reflector includes a first reflector disposed on another side wall of the cabinet, a second reflector disposed on a rear wall of the cabinet, and a third reflector disposed on the plate.

The shoe care apparatus may further include a machine compartment formed in a lower portion of the cabinet and communicating with the supply duct, and wherein the machine compartment includes a fan disposed in the machine compartment to lower the temperature of the sterilizer.

The shoe support device includes a case including a support frame protruding toward an inside of the shoe care compartment, a flow path communicating with the supply duct and formed in the case to allow air to move to the support frame and an air hole provided on an outer surface of the support frame and communicating with the flow path to supply air into the shoe care compartment, and wherein the air blown by the fan is discharged through the air hole to lower the temperature of the Ultraviolet lamp.

An aspect of the present disclosure provides a shoe care apparatus including a cabinet, a care compartment provided in the cabinet: a supply duct formed on one wall of the cabinet to supply air to the care compartment, a shoe support device communicating with the supply duct and coupled to an inner surface of one wall of the cabinet so that shoes are disposed in the care compartment, a sterilizer including an UV lamp to sterilize shoes disposed in the care compartment and disposed in the another wall of the cabinet, and a fan connected to the supply duct to blow air into the care compartment to lower the temperature of the ultraviolet lamp.

The shoe care apparatus further includes a machine compartment disposed a lower portion of the cabinet and configured to accommodate the fan, and communicates with the supply duct, and the shoe support device includes a case including a support frame protruding toward the inside of the care compartment, a flow path communicating with the supply duct and formed in the case so that air moves to the support frame and an air hole provided on the outer surface of the support frame and configured to communicate with the flow path to supply air into the care compartment, and the air blown by the fan may be discharged through the air hole to lower the temperature of the UV lamp.

The shoe care apparatus may further include a plate disposed below the shoe support device and at least one reflector disposed on at least one of a third wall of the cabinet and the plate to reflect ultraviolet rays emitted from the ultraviolet lamp.

The one wall is one side wall of the cabinet, the other wall is an upper wall of the cabinet, and the at least one reflector includes a first reflector disposed on the other side wall of the cabinet and a second reflector disposed on the rear wall of the cabinet and a third reflector disposed on the plate.

An aspect of the present disclosure provides a shoe care apparatus including a cabinet, a care compartment provided in the cabinet, a supply duct formed outside of one wall of the cabinet to supply air to the care compartment, a shoe support device configured to communicate with the supply duct to receive air from the supply duct and coupled to an inner surface of one side wall of the cabinet so that shoes are placed in the care compartment, a sterilizer including an UV lamp to sterilize shoes disposed in the care compartment and installed on an upper wall of the cabinet, and a plurality of reflectors disposed on the other side of the cabinet to reflect the ultraviolet rays emitted from the ultraviolet lamps.

The shoe care apparatus may further include a plate installed below the shoe support device and on which one of the plurality of reflectors is disposed.

BRIEF DESCRIPTION OF THE DRAWINGS

Aspects, features, and advantages of certain embodiments of the present disclosure will be more apparent from the following description taken in conjunction with the accompanying drawings, in which.

DETAILED DESCRIPTION

Figure 1:
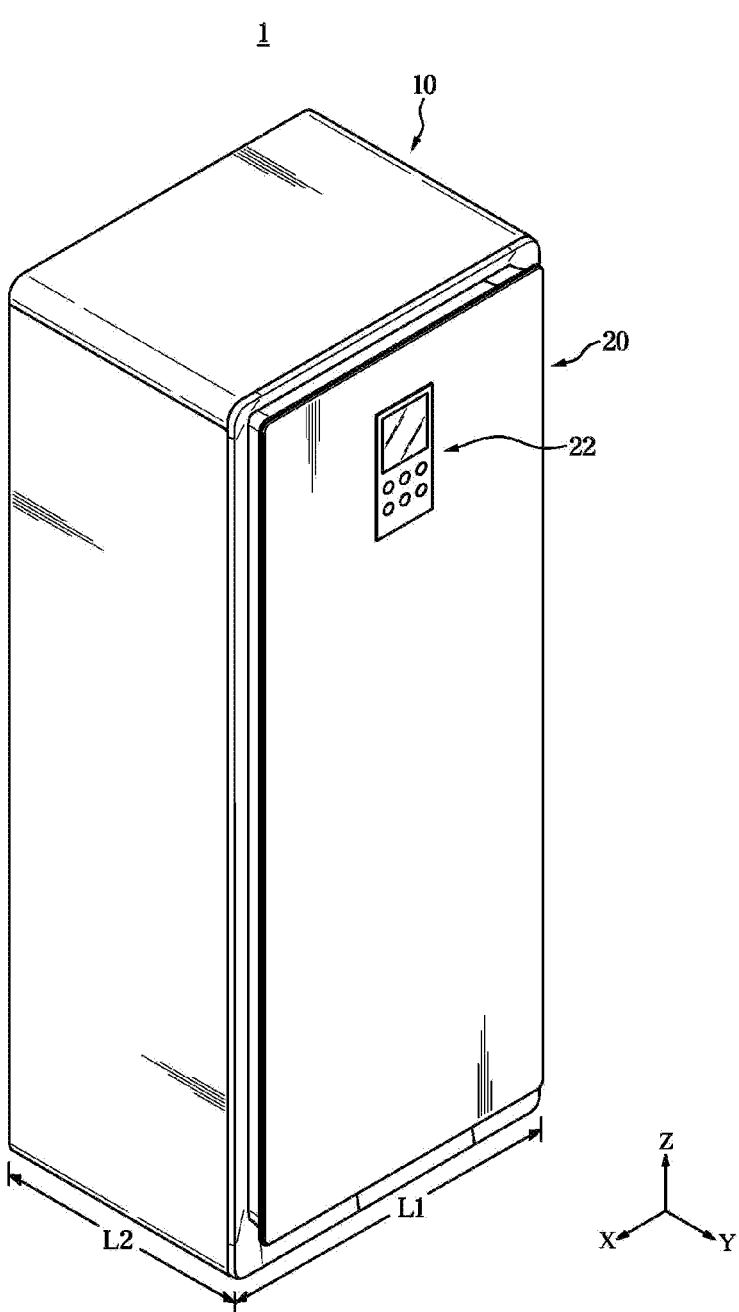
FIG. 1 is a view illustrating a shoe care apparatus according to an embodiment of the present disclosure.

The embodiments described in the present specification and the configurations shown in the drawings are only examples of preferred embodiments of the present disclosure, and various modifications may be made at the time of filing of the present disclosure to replace the embodiments and drawings of the present specification.

Like reference numbers or signs in the various drawings of the application represent parts or components that perform substantially the same functions.

The terms used herein are for the purpose of describing the embodiments and are not intended to restrict and/or to limit the present disclosure. For example, the singular expressions herein may include plural expressions, unless the context clearly dictates otherwise. Also, the terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that, although the terms first, second, etc. may be used herein to describe various components, these components should not be limited by these terms. These terms are only used to distinguish one component from another. For example, without departing from the scope of the present disclosure, the first component may be referred to as a second component, and similarly, the second component may also be referred to as a first component. The term "and/or" includes any combination of a plurality of related items or any one of a plurality of related items.

Terminology such as "at least one of A and B", as used herein, includes any of the following: A, B, A and B.

Terminology such as "at least one of A, B, and C", as used herein, includes any of the following: A, B, C, A and B, A and C, B and C, A and B and C.

In this specification, the terms "the front," "the rear," "the left side," and "the right side" used in the following description are defined with reference to the drawings, and the shape and position of each component are not limited by these terms.

Figure 2:
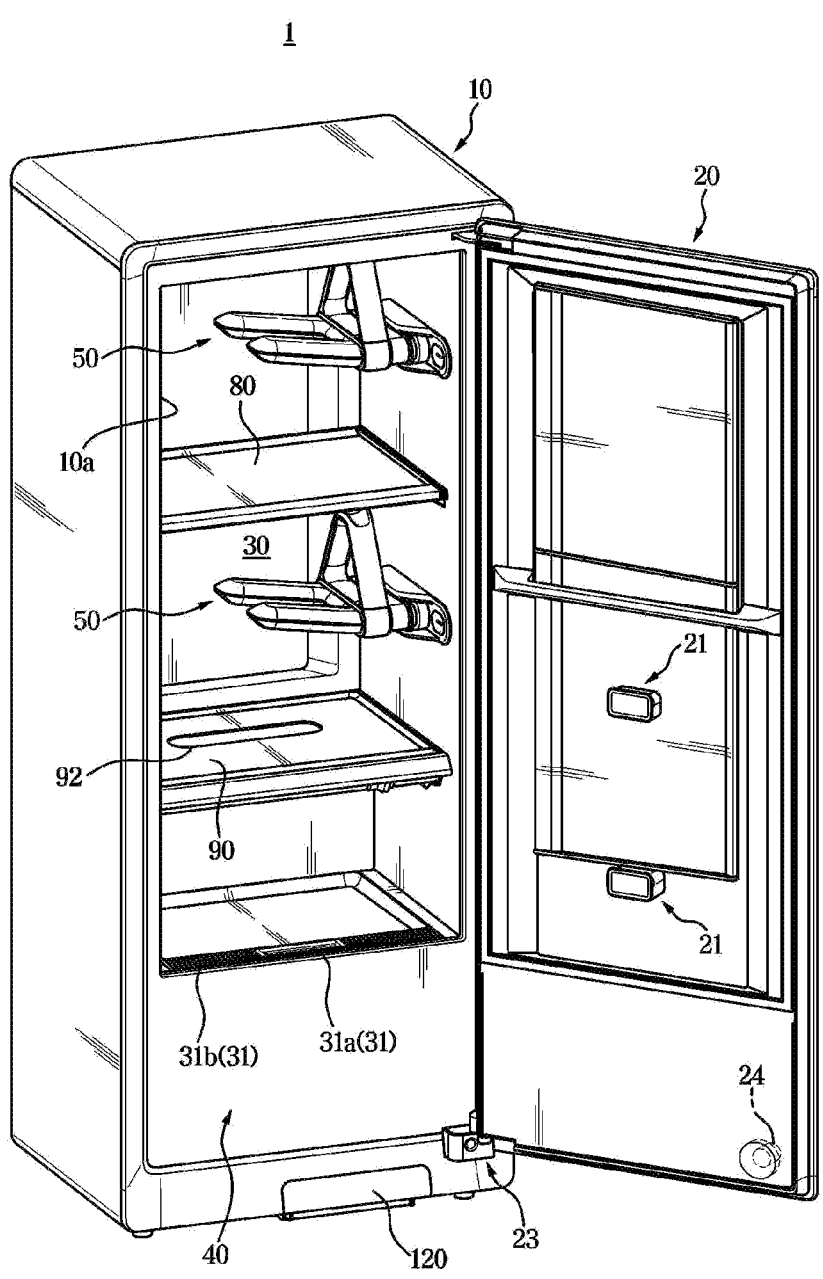
FIG. 2 is a perspective view illustrating that a door of the shoe care apparatus shown in FIG. 1 is opened.

Specifically, as shown in FIGS. 1 and 2, when a door of a shoe care apparatus is opened, a direction of directing to an inner surface is defined as the front, and based on this, the rear, left and right sides, and upper and lower sides are defined.

An aspect of various embodiments of the present disclosure provides a shoe care apparatus capable of effectively sterilizing shoes.

Another aspect of various embodiments of the present disclosure provides a shoe care apparatus including a sterilizer that reduces the possibility of injuring a user or adversely affecting the user.

Another aspect of various embodiments of the present disclosure provides a shoe care apparatus capable of easily controlling the temperature of the sterilizer.

According to various embodiments of the present disclosure, a shoe care apparatus that effectively sterilizes shoes through a sterilizer including an UV lamp can be provided.

Moreover, according to various embodiments of the present disclosure, a shoe care apparatus that reduces the possibility of injury to a user by adjusting the temperature of an UV lamp can be provided.

Further, according to various embodiments of the present disclosure, a shoe care apparatus with a reduced production cost can be provided.

Hereinafter, embodiments of the present disclosure will be described in detail with reference to the accompanying drawings.

The shoe care apparatus may include various apparatuses for dehumidifying a certain space, such as a clothes care apparatus or a shoe care apparatus. However, for convenience of description, the shoe care apparatus will be described below.

Figure 3:
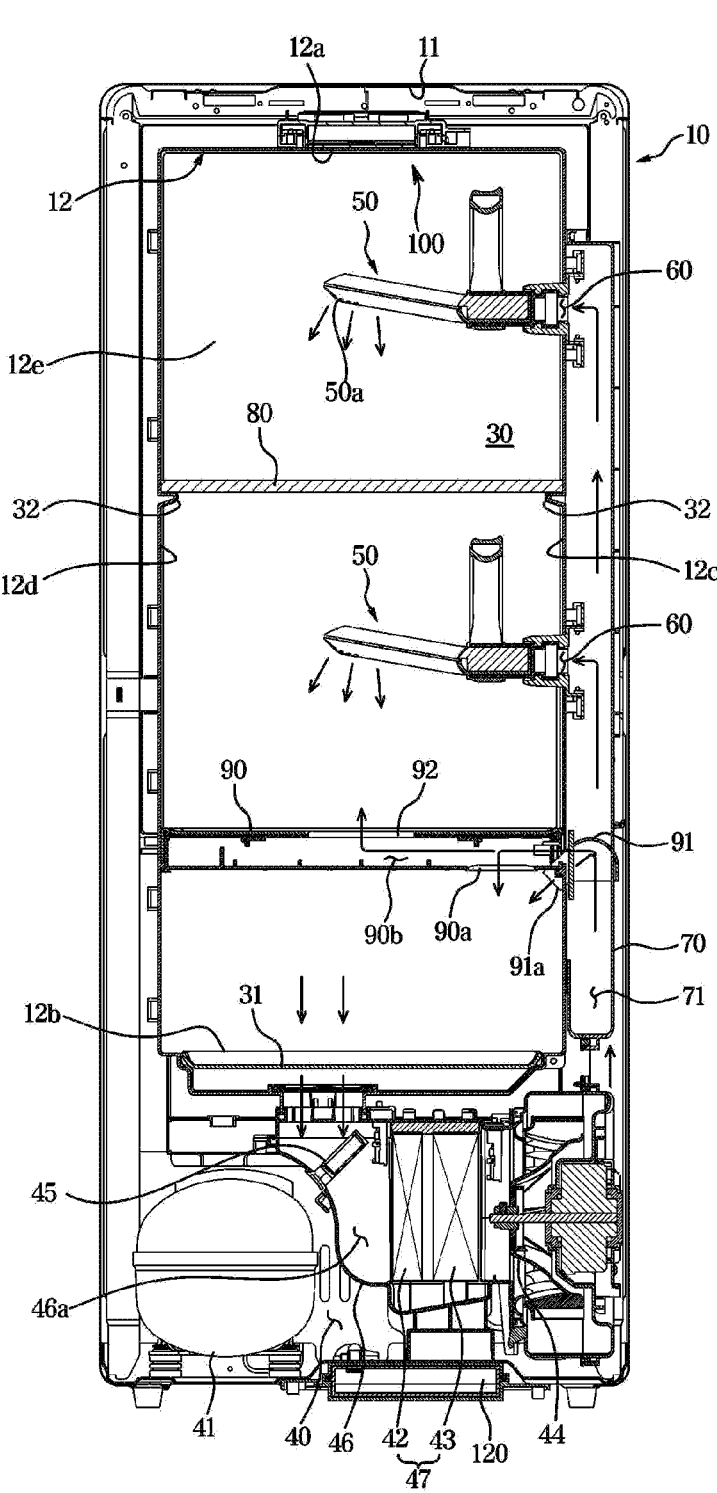
FIG. 3 is a front cross-sectional view of the shoe care apparatus shown in FIG. 1.

FIG. 1 is a view illustrating a shoe care apparatus according to an embodiment of the present disclosure. FIG. 2 is a perspective view illustrating that a door of the shoe care apparatus shown in FIG. 1 is opened. FIG. 3 is a front cross-sectional view of the shoe care apparatus shown in FIG. 1.

Referring to FIGS. 1 to 3, a shoe care apparatus 1 may include a main body 10 forming an exterior and a door 20 rotatably coupled to the main body 10.

The main body 10 may be provided in a rectangular parallelepiped shape with an open front side. An opening 10a may be formed in the open front side of the main body 10. The door 20 may be rotatably coupled to the main body 10 to open and close the open front side of the main body 10. The door 20 may be coupled to the main body 10 through a hinge 23 or the like.

The door 20 may include a hanging member 21 provided on a surface facing the inside of a shoe care compartment 30. One or more of the hanging members 21 may be provided. The hanging member 21 may easily store a shoe support device 50 by hanging a handle 55 of the shoe support device 50, which will be described later. However, the hanging member is not limited thereto and may be used for hanging other components.

The door 20 may further include a display 22 provided on a front surface of the shoe care apparatus 1. A user may set a care course suitable for a shoe to the display 22 depending on the type of shoes to be cared for. Through this, it is possible to reduce damage to shoes by adjusting the temperature and humidity of the shoe care compartment 30.

An opening/closing detection sensor 24 for detecting opening/closing of the door 20 may be provided at a lower portion of the door 20. The opening/closing detection sensor 24 may be a reed switch. However, it is not limited thereto and may include various types of sensors. If the opening/closing detection sensor 24 is a reed switch, magnetic force may be maintained when the door is closed, and magnetic force may be cut off when the door is opened. Through this, a processor (not shown) may determine opening and closing of the door 20. In the drawings, the opening/closing detection sensor 24 is illustrated as being located below the door 20, but it is not limited thereto and may be disposed in various locations. In addition, an additional opening/closing detection sensor 24 may be disposed inside the main body 10 as well.

The main body 10 may include an outer cabinet 11 and an inner cabinet 12 disposed inside the outer cabinet 11. The inner cabinet 12 may be referred to as a cabinet.

The main body 10 may be provided so that a length of a front surface extending in a first direction X and a length of a side surface extending in a second direction Y are different from each other. That is, a length L1 of the front surface may be longer than a length L2 of the side surface. Due to this, even in a narrow hallway, the shoe care apparatus 1 may be easily installed. The length of the front surface may be the first length L1, and the length of the side surface may be the second length L2.

The shoe care apparatus 1 may include the shoe support device 50 provided inside the shoe care compartment 30 to support the shoe.

The shoe care compartment 30 may form a space in which the shoes are accommodated. The shoe care compartment 30 may be provided inside the inner cabinet 12. The shoe care compartment 30 may be referred to as a treatment compartment 30.

The inner cabinet 12 may include a frame (not shown) provided to support an upper wall 12a, a lower wall 12b, a left wall 12c, a right wall 12d, and a rear wall 12e.

The shoe care compartment 30 provided to care for shoes may be provided in the inner cabinet 12.

The shoe care apparatus 1 may include a machine compartment 40 provided with a heat exchanger 47 for dehumidifying or heating the air inside the shoe care compartment 30 and like. The machine compartment 40 may be disposed under the care compartment 30.

The shoe support device 50 may be installed on the left wall 12c or the right wall 12d of the shoe care compartment 30. That is, the shoe support device 50 may be installed so that a side of the shoe is visible when viewed from the front of the shoe care apparatus 1. Due to this, the length of the side surface may be formed shorter.

The shoe support device 50 may be detachably installed to the shoe care compartment 30. One or more of the shoe support devices 50 may be provided. The shoe support device 50 may be formed in a shape in which the shoe may be fitted.

A drain container 48 provided detachably from the main body 10 may be installed at a lower portion of the main body 10. The drain container 48 may be disposed below the machine compartment 40 to facilitate the treatment of condensed water by the heat exchanger 47.

The machine compartment 40 may be provided at a lower side of the main body 10. The machine compartment 40 may be provided below the shoe care compartment 30. The drain container 48 may be provided below the machine compartment 40.

The heat exchanger 47 may be provided to dehumidify and heat air inside the shoe care compartment 30 as necessary.

The heat exchanger 47 may be installed to supply heated air into the shoe care compartment 30. The heat exchanger 47 may include an evaporator 42, a condenser 43, and a compressor 41 through which a refrigerant circulates, and may be provided to dehumidify and heat air.

As the refrigerant evaporates in the evaporator 42 of the heat exchanger 47 to absorb latent heat of the surrounding air, moisture in the air may be condensed and removed.

While the refrigerant is condensed in the condenser 43 via the compressor 41, the surrounding air may be heated by releasing the latent heat toward the surrounding air.

The evaporator 42 and the condenser 43 perform a heat exchange function, so that the air introduced into the machine compartment 40 by a blowing fan 44 may sequentially pass through the evaporator 42 and the condenser 43 to be dehumidified and heated.

The blowing fan 44 may be provided as a centrifugal fan that sucks air in an axial direction and discharges the air toward a supply duct 70. However, the blowing fan is not limited thereto.

The heat exchanger 47 installed in the machine compartment 40 may include a connection duct 46 to connect the evaporator 42, the condenser 43, and the blowing fan 44, and the connection duct 46 may be connected to the shoe care compartment 30 to form a connection flow path 46a circulating between the shoe care compartment 30 and the connection duct 46.

The shoe care apparatus 1 may further include a water supply container (not shown), a steam generator (not shown), and a steam injector (not shown). The water supply container may be disposed below the shoe care compartment 30. Water in the water supply container may be supplied to the steam generator and used to generate steam. The water supply container may be detachably installed on the main body to facilitate water replenishment.

The machine compartment 40 may be provided with the steam generator to generate steam by receiving water from the water supply container.

The steam generator may receive water by being connected to a water supply container to generate steam, and may include a steam supply pipe (not shown) to guide the generated steam to the steam injector (not shown).

The evaporator 42, the condenser 43, and the blowing fan 44 may be arranged in the first direction X so that air flows in the first direction X. The steam generator may also be arranged along the first direction X. Because the length of the side surface may be reduced as the evaporator 42, the condenser 43, the blowing fan 44 and the steam generator are all arranged in the first direction X, the shoe care apparatus may be easily installed in the hallway. The shoe care apparatus 1 may further include a deodorizer 45. The deodorizer 45 may be disposed in the machine compartment 40. The deodorizer 45 may be disposed in the connection duct 46 to remove odors in the air passed through the shoe care compartment 30. Although the drawing shows that the deodorizer 45 is provided on the right side of the blowing fan 44, the present disclosure is not limited thereto, and the deodorizer 45 may also be provided on the left side of the blowing fan 44.

The deodorizing device 45 may include a ceramic filter. However, it is not limited thereto, and the deodorizing device 45 may include various filters as long as they can remove odors in the air.

The shoe care apparatus I may include at least one plate 80. The plate 80 may be disposed in the shoe care compartment 30 to place shoes thereon.

The plate 80 may include a duct plate 90. As shown in FIG. 3, the duct plate 90 may include an inner flow path 90*b*. The heated air passing through the inner flow path 90*b* may be injected toward the shoes from an injection port 90*a* of the duct plate 90 and an injection port 91*a* of a circular duct 91. The heated air may be introduced into the shoe care compartment 30 through an inlet of the shoe support device 50 via the inner flow path 90*b*.

The shoe care device 1 may include a support protrusion 32. The support protrusion 32 may be provided so that the plate 80 is disposed within the shoe care compartment 30. The support protrusion 32 may support the plate 80 so as not to fall. For example, the support protrusion 32 may protrude toward the inside of the shoe care compartment 30 from inner surfaces of the left wall 12*c* and the right wall 12*d*. A plurality of support protrusions 32 may be provided.

The shoe care apparatus 1 may further include a supply port 60 and an outlet 31.

The supply port 60 may be formed on a side wall of the inner cabinet 12. That is, the supply port 60 may be formed on the left wall 12*c* of the shoe care compartment 30. However, the present disclosure is not limited thereto, and the supply port may be formed on the right wall 12*d*. One or more of the supply ports 60 may be formed to supply heated air into the shoe care compartment 30 to dry the shoes. The shape of the supply port 60 may be circular. However, the present disclosure is not limited thereto, and as long as the shoes may be dried by supplying the heated air into the shoe care compartment 30, the supply port may include various shapes such as a rectangle and a polygon.

The outlet 31 may be disposed in front of the lower wall 12*b* of the shoe care compartment 30. However, the location of the outlet 31 is not limited thereto. Air drying shoes in the shoe care compartment 30 may flow through the outlet 31 to the connection duct 46 which will be described later The outlet 31 may include a discharge hole 31*a* and a discharge grill 31*b*. However, the present disclosure is not limited thereto, and as long as the heated air may be smoothly supplied to the connection duct 46, the above components may be omitted.

The connection duct 46 may be connected to the supply duct 70 and the outlet 31 of the shoe care compartment 30. One end of the connection duct 46 may be connected to the supply duct 70, and the other end of the connection duct 46 may be connected to the outlet 31. The air introduced through the outlet 31 may be dehumidified and reintroduced into the shoe care compartment 30 through the supply duct 70 and the supply port 60.

The supply duct 70 may be provided on the outside of the side wall of the inner cabinet 12 in the second direction Y so that the front surface of the shoe care apparatus 1 is long and the side surface of the shoe care apparatus is short. One end of the supply duct 70 may be connected to the at least one supply port 60, and the other end thereof may be connected to the connection duct 46. The supply duct 70 may form a supply flow path 71 provided to move the heated air to the supply port 60.

The shoe care apparatus 1 may further include the shoe support device 50.

The shoe support device 50 may be detachably mounted on an inner surface of the side wall of the inner case 12. That is, the shoe support device 50 may be disposed on the left wall 12*c* of the shoe care compartment 30. However, the present disclosure is not limited thereto, and as long as the heated air may be supplied, the shoe support device may be disposed on the right wall 12*d* of the shoe care compartment 30.

The shoe support device 50 may be detachably coupled to the inner cabinet 12. Therefore, when a shoe hanging device (not shown) for long boots is installed in the shoe care compartment 30 or shoes are placed on the plate 80, the shoe support device 50 may be separated to utilize space.

The shoe care apparatus may include a sterilizer 100. The sterilizer 100 may be installed on the upper wall 12*a* of the inner cabinet. For example, the sterilizer 100 may be disposed between the outer cabinet 11 and the inner cabinet 12. Therefore, the sterilizer 100 may not be exposed to the outside, and the aesthetics of the shoe care device can be improved.

The sterilizer 100 may sterilize the outer skin of the shoe mounted on the shoe support device 50. Accordingly, shoes placed in the care compartment can be sterilized. The sterilizer 100 may be disposed on the upper wall 12*a* to sterilize shoes. However, the location of the sterilizer 100 is not limited to the above example. Accordingly, the sterilizer 100 may be disposed on the left wall 12*c* or the right wall 12*d*. In addition, the sterilizer may be disposed on the rear wall 12*e* or may be disposed on the door. The sterilizer 100 may be installed on any wall other than the wall where the shoe support device 50 is installed. Since the sterilizer 100 can be placed in various positions within the shoe care device, it is possible to freely utilize the space of the shoe care apparatus.

The machine compartment 40 may be provided below the care compartment 30. A fan 44 for sucking in air and blowing cooling air toward the supply duct 70 may be disposed in the machine compartment 40. The air blown by the fan 44 may pass through the supply duct 70 and flow to the shoe support device 50. Cooling air may be discharged to the care compartment 30 through the air hole 50*a* provided in the shoe support device 50. Cooling air can control the temperature of the overheated UV lamp 120. Therefore, in case of emergency, it is possible to prevent the user from being injured due to the overheated UV lamp 120.

Figure 4:
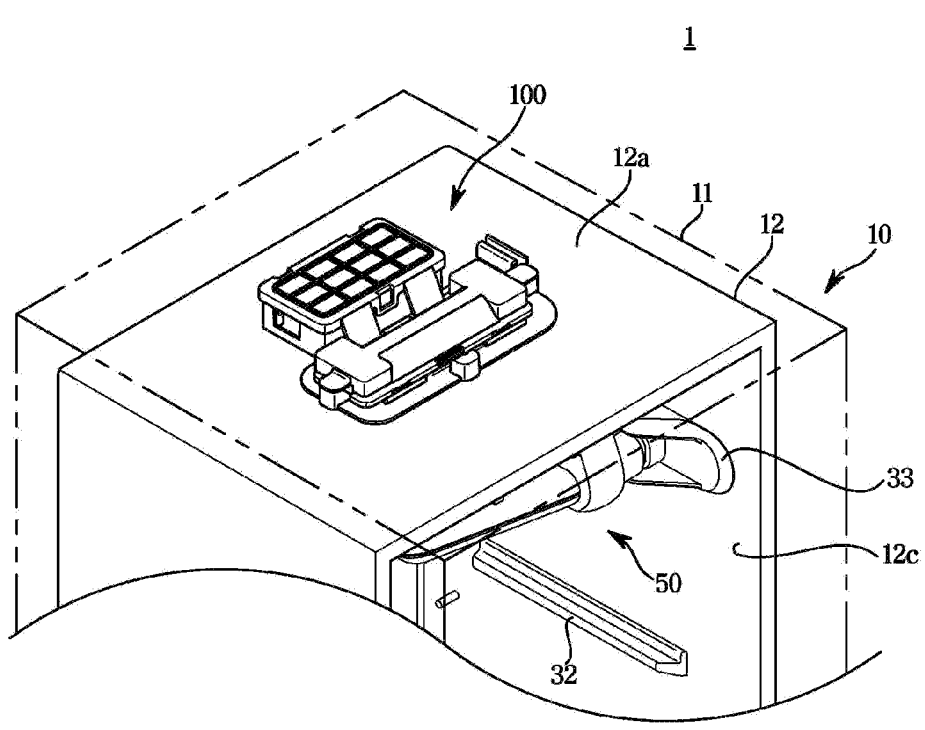
FIG. 4 is a perspective view illustrating a sterilizer and components related to the sterilizer of the shoe care apparatus shown in FIG. 1.
Figure 5:
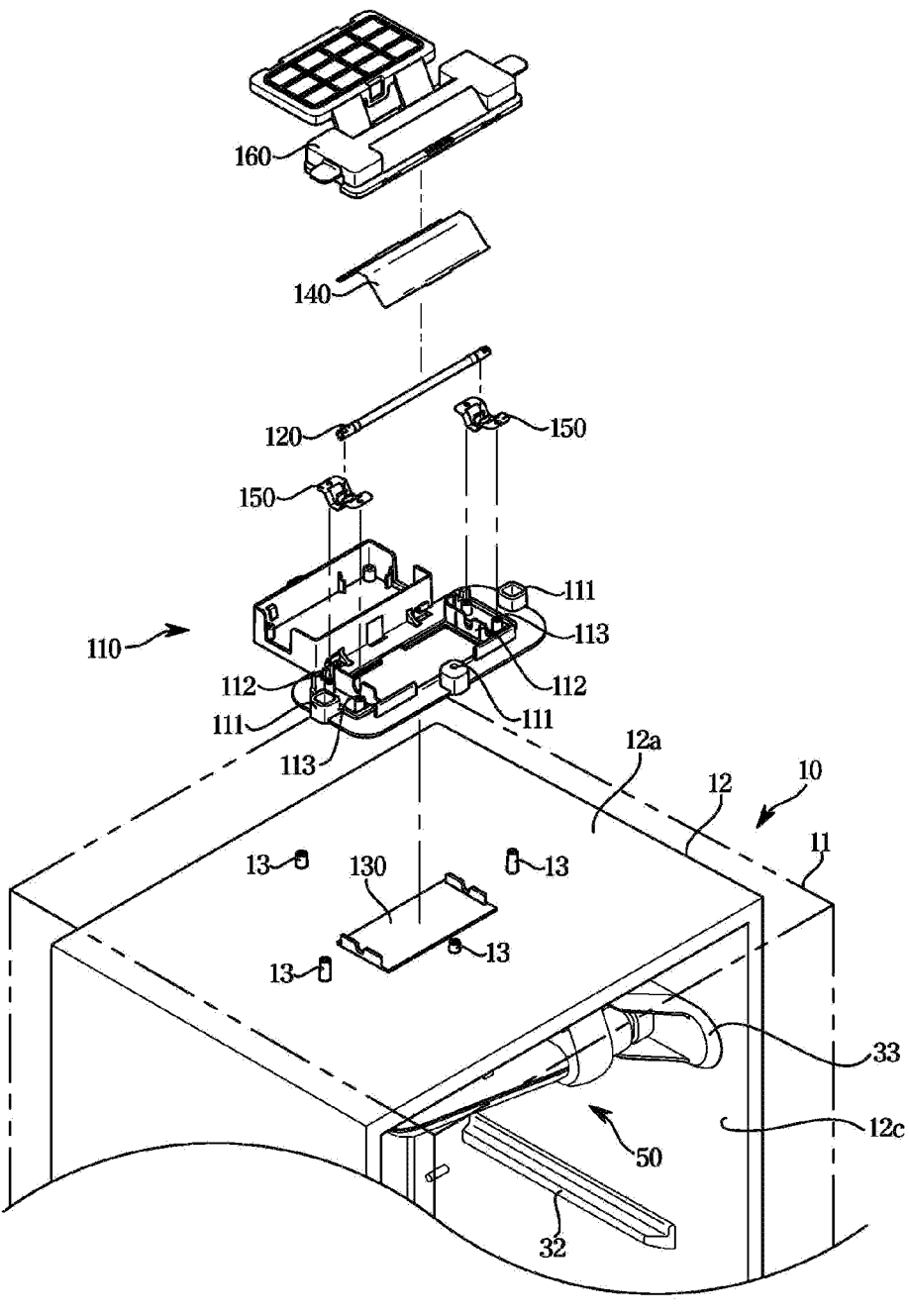
FIG. 5 is an exploded view showing the sterilizer of the shoe care apparatus shown in FIG. 4.

FIG. 4 is a perspective view illustrating a sterilizer components related to the sterilizer of the shoe care apparatus shown in FIG. 1. FIG. 5 is an exploded view showing the sterilizer of the shoe care apparatus shown in FIG. 4.

Referring to FIGS. 4 and 5, the main body 10 may include an outer cabinet 11 and an inner cabinet 12. The sterilizer 100 may be installed on the upper wall 12*a* of the inner cabinet 12. For example, the sterilizer 100 may be disposed between the outer cabinet 11 and the inner cabinet 12.

The sterilizer 100 may include cases 110 and 160, an ultraviolet (UV) lamp) 120, a protective plate 130, a reflective member 140, and a bracket 150.

The cases 110 and 160 may be provided to accommodate the UV lamp 120, the protective plate 130, the reflective member 140, and the bracket 150. The cases 110 and 160 may include a first case 110 and a second case 160. The first case 110 may be the lower case 110 and the second case 160 may be the upper case 160. For example, the first case 110 may be disposed below the UV lamp 120 to accommodate the UV lamp 120, the second case 160 may be disposed above the UV lamp 120 to accommodate the UV lamp 120.

The first case 110 may be coupled to the upper wall 12*a*. The first case 110 may be coupled to a coupling protrusion 13 provided on the upper wall 12*a*. The first case 110 may include an upper wall coupling portion 111, a seating groove 112, and a bracket coupling portion 113.

The upper wall coupling portion 111 may be provided in a shape corresponding to the coupling protrusion 13 provided on the upper wall 12*a*. For example, the upper wall coupling portion 111 may be provided in a hole or groove shape. However, the shape of the upper wall coupling portion 111 is not limited thereto. The seating groove 112 may be recessed so that the UV lamp 120 and the bracket 150 can be seated. The seating groove 112 may be provided in a shape corresponding to the UV lamp 120 and the bracket 150. For example, the seating groove 112 may be circularly recessed to correspond to a cylindrical shape. However, the shape of the seating groove 112 is not limited thereto. The bracket coupling portion 113 may be provided in a shape corresponding to the bracket 150 to be coupled with the bracket 150. For example, the bracket coupling portion 113 may be provided as a protrusion. However, the shape of the bracket coupling portion 113 is not limited thereto. The bracket coupling portion 113 may be provided corresponding to the number of brackets 150. For example, the bracket coupling portion 113 may be provided in two.

The UV lamp 120 may be disposed in the cases 110 and 160 to emit ultraviolet rays to sterilize shoes. The UV lamp 120 may be provided in a cylindrical shape. However, the shape of the UV lamp 120 is not limited thereto. In addition, the UV lamp 120 may emit UVC. However, it is not limited thereto, and the UV lamp 120 may also emit UVA and UVB.

The bracket 150 may be coupled with the UV lamp 120 and the first case 110. The bracket 150 may be provided in plurality. For example, the bracket 150 may be coupled to both sides of the UV lamp 120. The bracket 150 may be coupled to the bracket coupling portion 113 of the first case 110. The bracket 150 and the bracket coupling portion 113 may be provided in corresponding shapes.

The protection plate 130 may be provided so that the user does not come into contact with the UV lamp 120 provided in the cases 110 and 160. For example, a hole through which ultraviolet rays are irradiated to the shoe may be provided in the upper wall 12*a*, and the protective plate 130 may be provided to close the hole. Thus, the protection plate 130 can prevent a user from being injured. The protective plate 130 may have a mesh shape or include a quartz glass material. However, the shape and material of the protective plate 130 are not limited to the above examples.

The reflective member 140 may reflect ultraviolet rays emitted from the UV lamp 120. The reflective member 140 may be disposed above the UV lamp 120. Accordingly, ultraviolet rays directed upward may be reflected downward through the reflective member 140, and ultraviolet rays of the UV lamp 120 may be directed only to shoes.

The second case 160 may be coupled with the first case 110 to accommodate the UV lamp 120 and the reflective member 140. The second case 160 may be coupled to the upper side of the first case 110.

Figure 6:
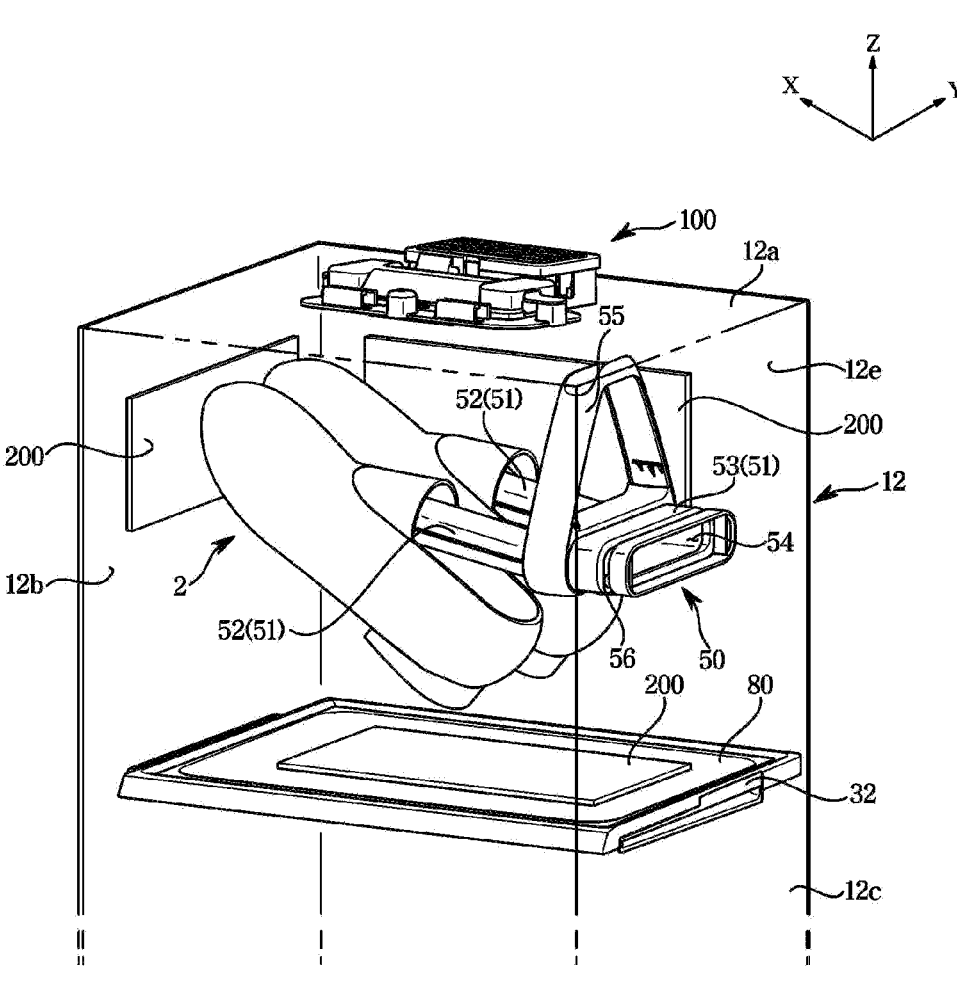
FIG. 6 is a perspective view of the shoe care apparatus shown in FIG. 4 from another angle.
Figure 7:
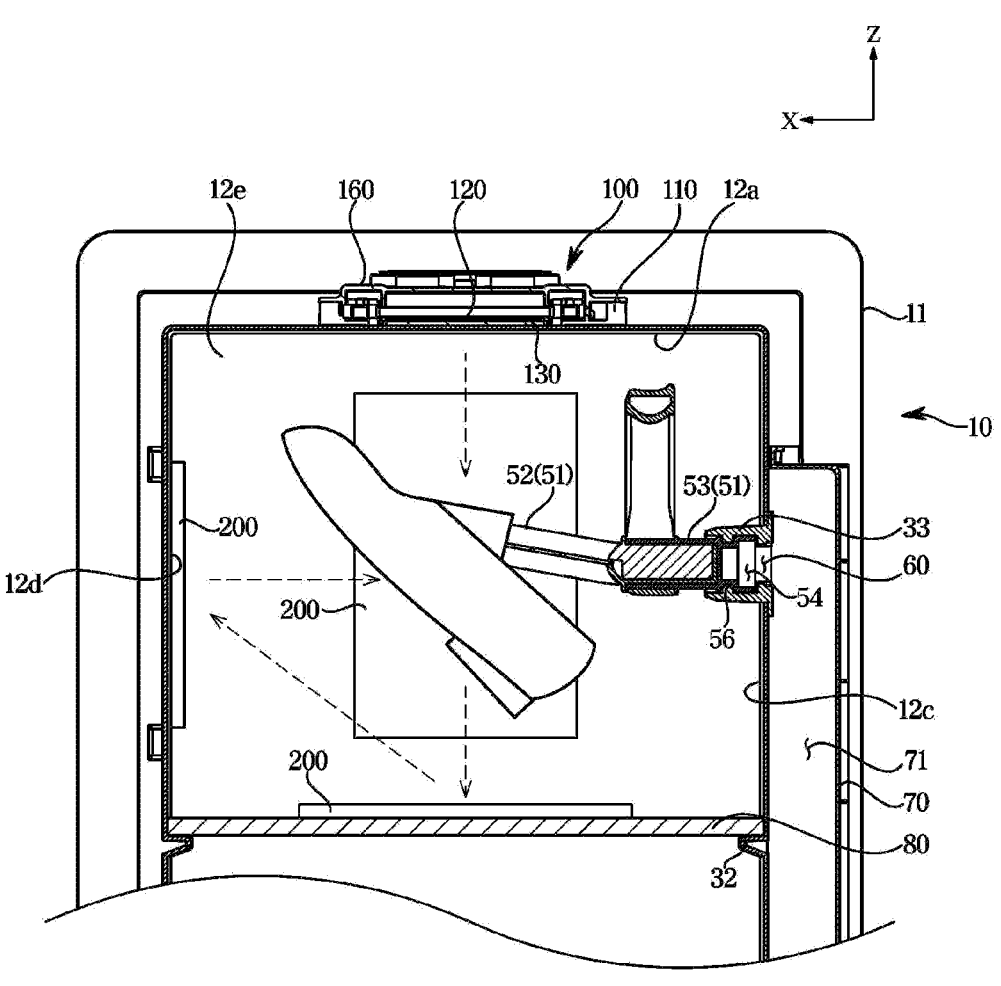
FIG. 7 is a front view of the shoe care apparatus shown in FIG. 6.

FIG. 6 is a perspective view of the shoe care apparatus shown in FIG. 4 from another angle. FIG. 7 is a front view of the shoe care apparatus shown in FIG. 6.

Referring to FIGS. 6 and 7, the shoe support device 50 may include a case 51, a flow path 54, a handle 55, and a mounting groove 56. The shoe support device 50 may be mounted to the left wall 12*c*.

The case 51 may include a support frame 52 and an extension 53. The support frame 52 may extend in a first direction X from the extension 53 so that the shoe may be supported. The support frame 52 may be provided in plurality. The plurality of support frames 52 may be spaced apart from each other along the second direction Y. Thus, a pair of shoes may be supported on a plurality of support frames 52. The extension 53 may extend from the support frames 52 toward the left wall 12*c* so that the shoe support device 50 is coupled to the inner cabinet 12.

The flow path 54 may be provided so that cooling air passing through the fan 44 and the supply duct 70 is sprayed through the air hole 50*a*. For example, the flow path 54 may be provided inside the case 51. Through this, the cooling air injected into the air hole 50*a* may lower the temperature of the UV lamp 120.

The handle 55 may be provided on the upper side of the extension 53 so that the user can move the shoe support device 50. The mounting groove 56 may be formed by being recessed so that the shoe support device 50 is mounted on a mounting portion 33.

The sterilizer 100 may be disposed between the plurality of support frames 52 in the second direction Y. In addition, the sterilizer 100 may be disposed in the middle of the inner cabinet 12 extending along the first direction X. For example, the sterilizer 100 may be disposed at the center of the upper wall 12*a*. Through this, it is possible to evenly sterilize the outer skins of the two pairs of shoes 2 spaced apart on both sides.

The shoe care apparatus may further include at least one reflector 200. The reflector 200 may reflect ultraviolet rays emitted from the UV lamp 120. For example, at least one reflector 200 may be attached to the right wall 12*d*, the rear wall 12*e* and the plate 80 disposed below the shoe support device 50. For example, the at least one reflector 200 includes a first reflector 200 disposed on the right wall 12*d*, a second reflector 200 disposed on the rear wall 12*e*, and a third reflector 200 disposed on the plate 80. Ultraviolet rays emitted from the UV lamp 120 may be emitted in multiple directions. For example, ultraviolet rays may pass between the plurality of support frames 52 and may be irradiated to at least one reflector 200. The ultraviolet rays emitted from the UV lamp 120 may be reflected through the reflector 200 so that the entire outer skin of the shoe 2 is irradiated with ultraviolet rays. Accordingly, the shoes 2 can be sterilized as a whole.

The foregoing has illustrated and described specific embodiments. However, it should be understood by those of skilled in the art that the disclosure is not limited to the above-described embodiments, and various changes and modifications may be made without departing from the technical idea of the disclosure described in the following claims.

What is claimed is:

1. A shoe care apparatus comprising:
   an outer cabinet;
   an inner cabinet inside the outer cabinet;
   a shoe care compartment inside the inner cabinet;
   a door configured to open and close the shoe care compartment;
   a supply duct between the inner cabinet and the outer cabinet to supply air to the shoe care compartment;
   a shoe support device installable on an inner side of a wall of the inner cabinet such that, with the shoe support device installed on the inner side of the wall of the inner cabinet,
      the shoe support device protrudes from the inner side of the wall of the inner cabinet into the shoe care compartment such that shoes are supportable on the shoe support device in the shoe care compartment, and the shoe support device is configured to communicate with the supply duct to receive the air from the supply duct and provide the air into the shoes supported on the shoe support device in the shoe care compartment; and a sterilizer disposed between the inner cabinet and the outer cabinet and on wall of the inner cabinet that is different than the wall of the inner cabinet on which the shoe support device is installable, or on the door, and including an ultraviolet (UV) lamp to sterilize outer skins of shoes supported on the shoe support device in the shoe care compartment.

2. The shoe care apparatus according to claim 1, wherein the shoe support device includes a plurality of support frames protruding in a first direction toward an inside of the shoe care compartment and spaced apart in a second direction, and the sterilizer is disposed between the plurality of support frames along the second direction.

3. The shoe care apparatus according to claim 2, wherein the sterilizer is disposed in a center of a wall of the inner cabinet that is different than the wall of the inner cabinet on which the shoe support device is installable.

4. The shoe care apparatus according to claim 1, wherein the wall of the inner cabinet on which the shoe support device is installable is a side wall of the inner cabinet; and the wall of the inner cabinet in which the sterilizer is disposed is an upper wall of the inner cabinet.

5. The shoe care apparatus according to claim 4, wherein the sterilizer includes:

a first case coupled to the upper wall of the inner cabinet and in which the UV lamp is seated, a protective plate accommodated in the first case and disposed below the UV lamp, a reflective member disposed above the UV lamp, and a second case disposed above the reflective member and configured to cover the reflective member and the UV lamp.

6. The shoe care apparatus according to claim 1, further comprising:

a plate horizontally disposed below the shoe support device in the shoe care compartment to support shoes in the shoe care compartment and that are not supported by the shoe support device; and a reflector on the plate to reflect ultraviolet rays irradiated from the UV lamp.

7. The shoe care apparatus according to claim 6, further comprising:

a reflector on an inner side of a wall of the inner cabinet that is different than the wall of the inner cabinet on which the shoe support device is installable.

8. The shoe care apparatus according to claim 1, further comprising:

a machine compartment below the shoe care compartment and communicating with the supply duct, wherein the machine compartment includes a fan disposed in the machine compartment to lower a temperature of the sterilizer.

9. The shoe care apparatus according to claim 8, wherein the shoe support device includes:

a case including a support frame protruding toward an inside of the shoe care compartment, a flow path communicating with the supply duct and formed in the case to allow air to move to the support frame, and an air hole provided on an outer surface of the support frame and communicating with the flow path to supply air into the shoe care compartment, and the air blown by the fan is discharged through the air hole to lower the temperature of the UV lamp.

10. The shoe care apparatus according to claim 1, wherein the shoe support device includes:

an extension configured to connect the shoe support device to the inner side of the wall of the inner cabinet, a support frame extending from the extension and configured to support the shoes, and a handle on a side of the extension to enable movement of the shoe support device.

* * * * *